US009618517B2

(12) United States Patent
Mackintosh et al.

(10) Patent No.: US 9,618,517 B2
(45) Date of Patent: *Apr. 11, 2017

(54) ANALYTE MEASUREMENT METHOD AND SYSTEM WITH ERROR TRAPPING

(75) Inventors: Stephen Mackintosh, Inverness (GB); David McColl, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 988 days.

This patent is subject to a terminal disclaimer.

(21) Appl. No.: 13/768,783

(22) PCT Filed: Sep. 28, 2011

(86) PCT No.: PCT/GB2011/001412
§ 371 (c)(1),
(2), (4) Date: May 7, 2013

(87) PCT Pub. No.: WO2012/042211
PCT Pub. Date: Apr. 5, 2012

(65) Prior Publication Data
US 2013/0217053 A1    Aug. 22, 2013

Related U.S. Application Data

(60) Provisional application No. 61/387,366, filed on Sep. 28, 2010.

(51) Int. Cl.
*G01N 33/66*        (2006.01)
*G01N 27/327*       (2006.01)

(52) U.S. Cl.
CPC .......... *G01N 33/66* (2013.01); *G01N 27/3274* (2013.01)

(58) Field of Classification Search
CPC .............. G01N 33/66; G01N 27/327–27/3274
See application file for complete search history.

(56) References Cited

U.S. PATENT DOCUMENTS

| 5,873,990 | A | 2/1999 | Wojciechowski et al. |
| 6,733,655 | B1 * | 5/2004 | Davies ............ C12Q 1/001 205/775 |
| 2006/0224658 | A1 | 10/2006 | Sato et al. |
| 2007/0074977 | A1 | 4/2007 | Guo et al. |

(Continued)

FOREIGN PATENT DOCUMENTS

| EP | 1447452 B1 | 12/2008 |
| EP | 1600773 B1 | 2/2009 |

(Continued)

OTHER PUBLICATIONS

Patent Examination Report No. 1 issued in related Australian Application No. 2011309958, dated Aug. 21, 2014, 5 pages.

(Continued)

*Primary Examiner* — Luan Van
*Assistant Examiner* — Maris R Kessel

(57) ABSTRACT

Described and illustrated herein are systems and exemplary methods of operating an analyte measurement system having a meter and a test strip. The methods and systems describe herein allow for trapping various errors during calculation of the analyte due to variations in the structure and materials making up the test strip and ambient temperatures.

25 Claims, 12 Drawing Sheets

(56) References Cited

U.S. PATENT DOCUMENTS

| 2007/0087397 | A1 | 4/2007 | Kraft et al. |
| 2009/0184004 | A1 | 7/2009 | Chatelier et al. |
| 2009/0322341 | A1 | 12/2009 | Kraft et al. |
| 2013/0095510 | A1 | 4/2013 | Malecha et al. |

FOREIGN PATENT DOCUMENTS

| JP | 2003526785 A | 9/2003 |
| JP | 2007108171 A | 4/2007 |
| JP | 2007114198 A | 5/2007 |
| JP | 2009168815 A | 7/2009 |
| JP | 2013524196 A | 6/2013 |
| WO | 2004011921 A1 | 2/2004 |
| WO | WO 2007/040913 A1 | 4/2007 |

OTHER PUBLICATIONS

First Office Action issued in related Chinese Patent Application No. 201180046843.X, dated Dec. 16, 2013, 16 pages.
Search Report issued in related Chinese Patent Application No. 201180046843.X, 3 pages.
Second Office Action issued in related Chinese Patent Application No. 201180046843.X, dated Oct. 27, 2014, 7 pages.
European Search Report issued in related European Patent Application No. 14165261.0, dated Jul. 30, 2014, 9 pages.
International Search Report and Written Opinion issued in related International Application No. PCT/GB2011/001412, mailed Mar. 29, 2012, 18 pages.
European Search Report issued in related European Patent Application No. 11769901.7, dated Jun. 6, 2014, 5 pages.
Notice of Reasons for Rejection issued in related Japanese Patent Application No. 2013-529703, transmitted on May 26, 2015, 8 pages.

\* cited by examiner

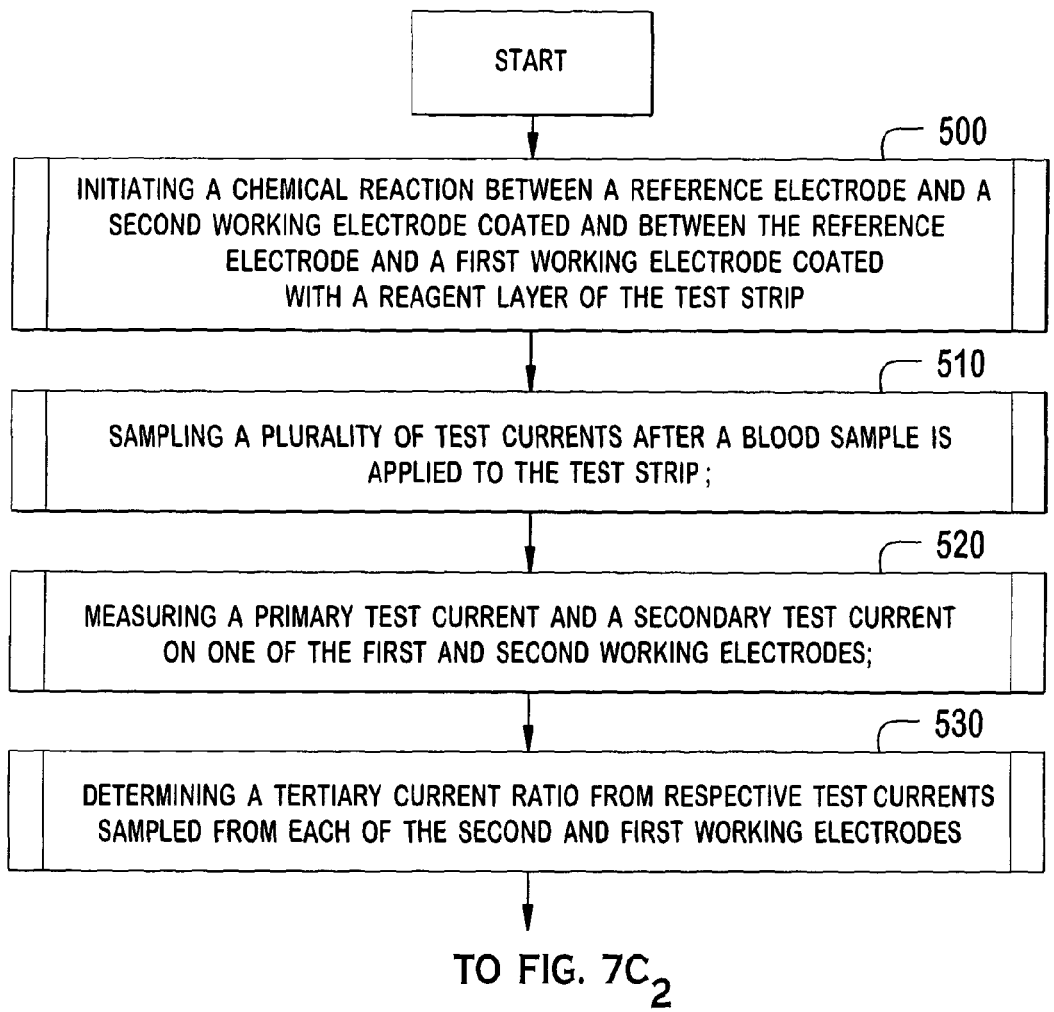
FIG. 7C₁

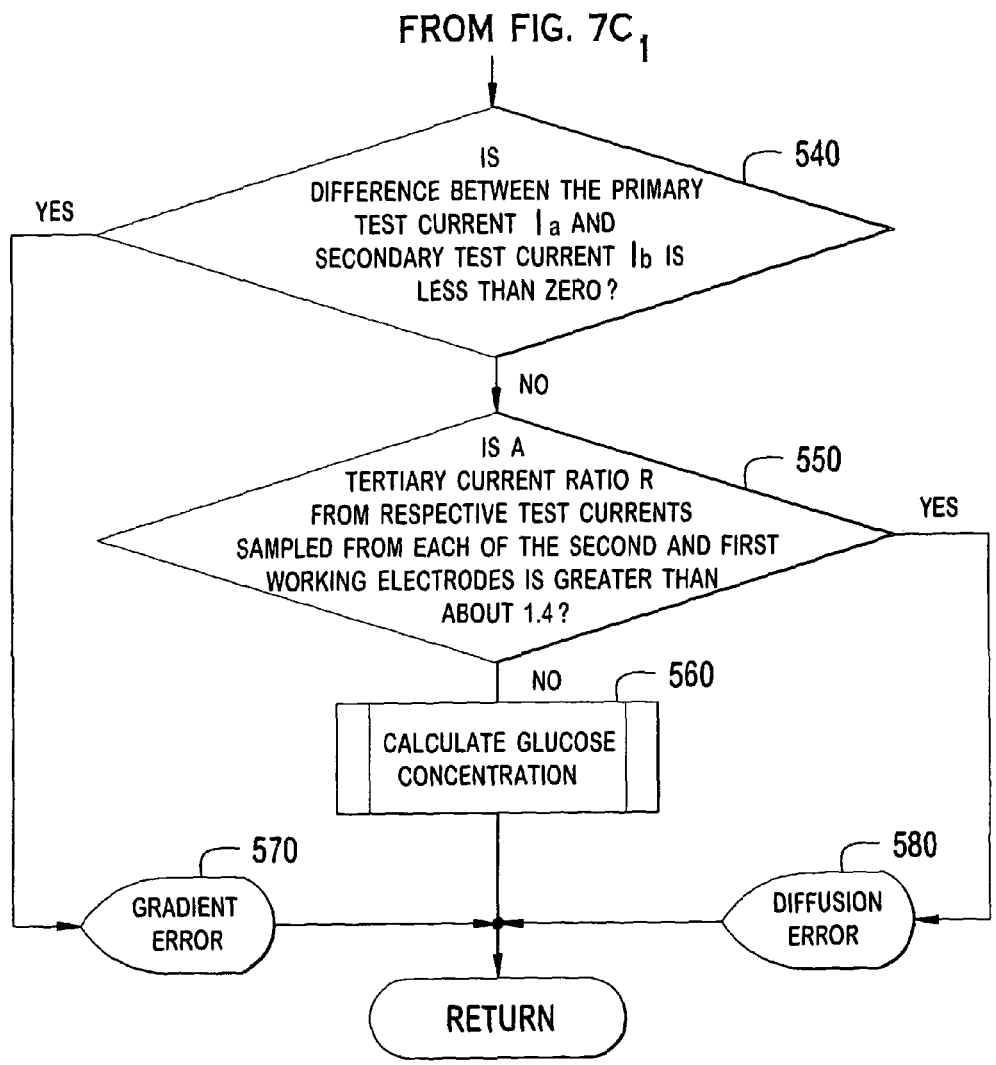
FIG. 7C₂

ANALYTE MEASUREMENT METHOD AND SYSTEM WITH ERROR TRAPPING

This application claims the benefits of priority under one or more of the Paris Convention, 35 USC§§119, 120, or 365 to U.S. Provisional Patent Application 61/387,366, filed on Sep. 28, 2010, titled "ANALYTE MEASUREMENT METHOD AND SYSTEM WITH ERROR TRAPPING" which application is incorporated by reference in its entirety herein.

BACKGROUND

Electrochemical sensors have been used to detect or measure the presence of substances in fluid samples. Electrochemical sensors include a reagent mixture containing at least an electron transfer agent (also referred to as an "electron mediator") and an analyte specific bio-catalytic protein (e.g. a particular enzyme), and one or more electrodes. Such sensors rely on electron transfer between the electron mediator and the electrode surfaces and function by measuring electrochemical redox reactions. When used in an electrochemical biosensor system or device, the electron transfer reactions are monitored via an electrical signal that correlates to the concentration of the analyte being measured in the fluid sample.

The use of such electrochemical sensors to detect analytes in bodily fluids, such as blood or blood derived products, tears, urine, and saliva, has become important, and in some cases, vital to maintain the health of certain individuals. In the health care field, people such as diabetics, for example, must monitor a particular constituent within their bodily fluids. A number of systems are capable of testing a body fluid, such as, blood, urine, or saliva, to conveniently monitor the level of a particular fluid constituent, such as, cholesterol, proteins, and glucose. Patients suffering from diabetes, a disorder of the pancreas where insufficient insulin production prevents the proper digestion of sugar, have a need to carefully monitor their blood glucose levels on a daily basis. Routine testing and controlling blood glucose for people with diabetes can reduce their risk of serious damage to the eyes, nerves, and kidneys.

SUMMARY OF THE DISCLOSURE

Applicants have recognized a need for a system and method that can be used to determine an accurate glucose concentration that avoids the disadvantages in the field. In view of the foregoing and in accordance with one aspect, there is provided a method for determining a glucose concentration with a system having a test strip and a meter. The test strip may include a reference electrode, a first working electrode and a second working electrode in which the first electrodes are coated with a reagent layer. The meter may include an electronic circuit for applying a test voltage between the reference electrode and the first working electrode and for applying a second test voltage between the reference electrode and the second working electrode. The meter also may include a signal processor for measuring a plurality of test currents and for calculating a glucose concentration from the test currents. The method can be achieved by: initiating a chemical reaction between a reference electrode and a second working electrode coated with a reagent layer and between the reference electrode and a first working electrode coated with a reagent layer of the test strip; measuring a primary test current and a secondary test current on one of the first and second working electrodes; determining whether a difference between the primary test current and secondary test current is less than zero; and upon the determining being true, deriving or calculating a glucose concentration based on the plurality of test currents else otherwise returning an error.

In yet a further embodiment, a method for determining a glucose concentration with a system having a test strip and a meter. The test strip may include a reference electrode, a first working electrode and a second working electrode in which the first electrodes are coated with a reagent layer. The meter may include an electronic circuit for applying a test voltage between the reference electrode and the first working electrode and for applying a second test voltage between the reference electrode and the second working electrode. The meter also may include a signal processor for measuring a plurality of test currents and for calculating a glucose concentration from the test currents. The method can be achieved by: initiating a chemical reaction between a reference electrode and a second working electrode coated with a reagent layer and between the reference electrode and a first working electrode coated with a reagent layer of the test strip; sampling a plurality of test currents after a blood sample is applied to the test strip; determining a current ratio from respective tertiary test currents sampled from each of the second and first working electrodes; and querying as to whether the current ratio of the second working electrode to the first working electrode is less than K, and if true, deriving or calculating a glucose concentration based on the plurality of test currents else otherwise returning an error.

In another embodiment, a method for determining a glucose concentration with a system having a test strip and a meter. The test strip may include a reference electrode, a first working electrode and a second working electrode in which the first electrodes are coated with a reagent layer. The meter may include an electronic circuit for applying a test voltage between the reference electrode and the first working electrode and for applying a second test voltage between the reference electrode and the second working electrode. The meter also may include a signal processor for measuring a plurality of test currents and for calculating a glucose concentration from the test currents. The method can be achieved by: initiating a chemical reaction between a reference electrode and a second working electrode coated with a reagent layer and between the reference electrode and a first working electrode coated with a reagent layer of the test strip; measuring a primary test current and a secondary test current on one of the first and second working electrodes; determining whether a difference between the primary test current and secondary test current is less than zero; determining a current ratio from respective tertiary test currents sampled from each of the second and first working electrodes; evaluating whether a current ratio from respective tertiary test currents sampled from each of the second and first working electrodes is greater than K; and upon either or both of the determining step or evaluating step being true, returning an error otherwise deriving or calculating a glucose concentration based on the plurality of test currents.

These and other embodiments, features and advantages of the invention will become apparent to those skilled in the art when taken with reference to the following more detailed description of the exemplary embodiments in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (in which like numerals represent like elements), of which:

FIG. 7C illustrates a method that combines both techniques of FIGS. 7A and 7B.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Figure 1A:
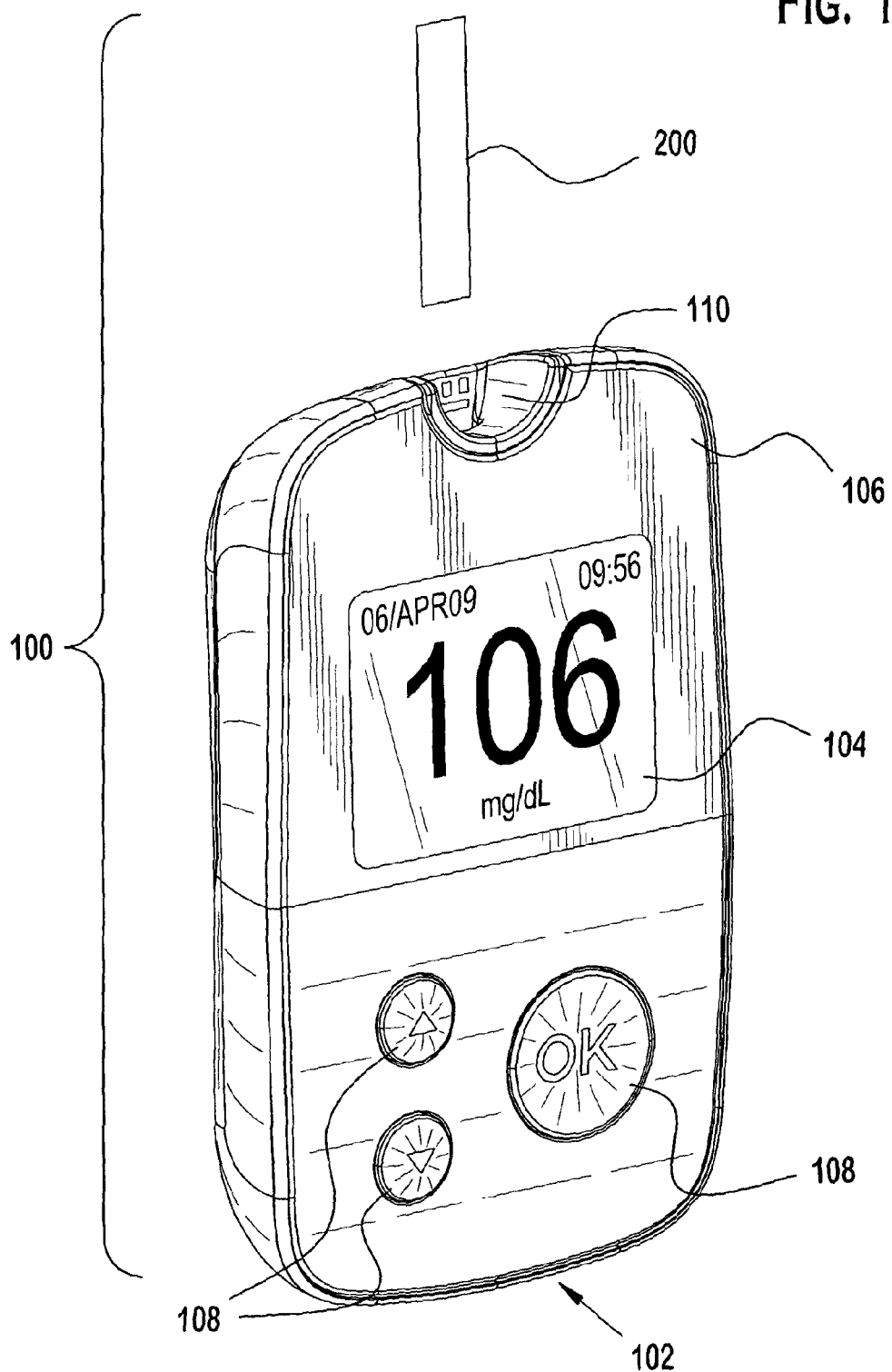
FIG. 1A illustrates an exemplary embodiment of a top view of a system for measuring an analyte concentration.

FIG. 1A illustrates a system 100 for measuring an analyte concentration in which system 100 may include a meter 102 and a test strip 120. Meter 102 may include a display 104, a housing 106, a plurality of user interface buttons 108, and a strip port 110. Meter 102 further may include electronic circuitry within housing 106 as further described in relation to FIG. 1B. A proximal portion of test strip 120 may be inserted into strip port 110. Display 104 may annunciate an analyte concentration, e.g., glucose concentration, and may be used to show a user interface for prompting a user on how to perform a test. As used here, the term "annunciate" and variations on the root term indicate that an announcement may be provided via text, audio, visual or a combination of all modes of communication to a user, a caretaker of the user, or a healthcare provider. The plurality of user interface buttons 108 allow a user to operate meter 102 by navigating through the user interface software. Display 104 may optionally include a backlight.

Figure 1B:
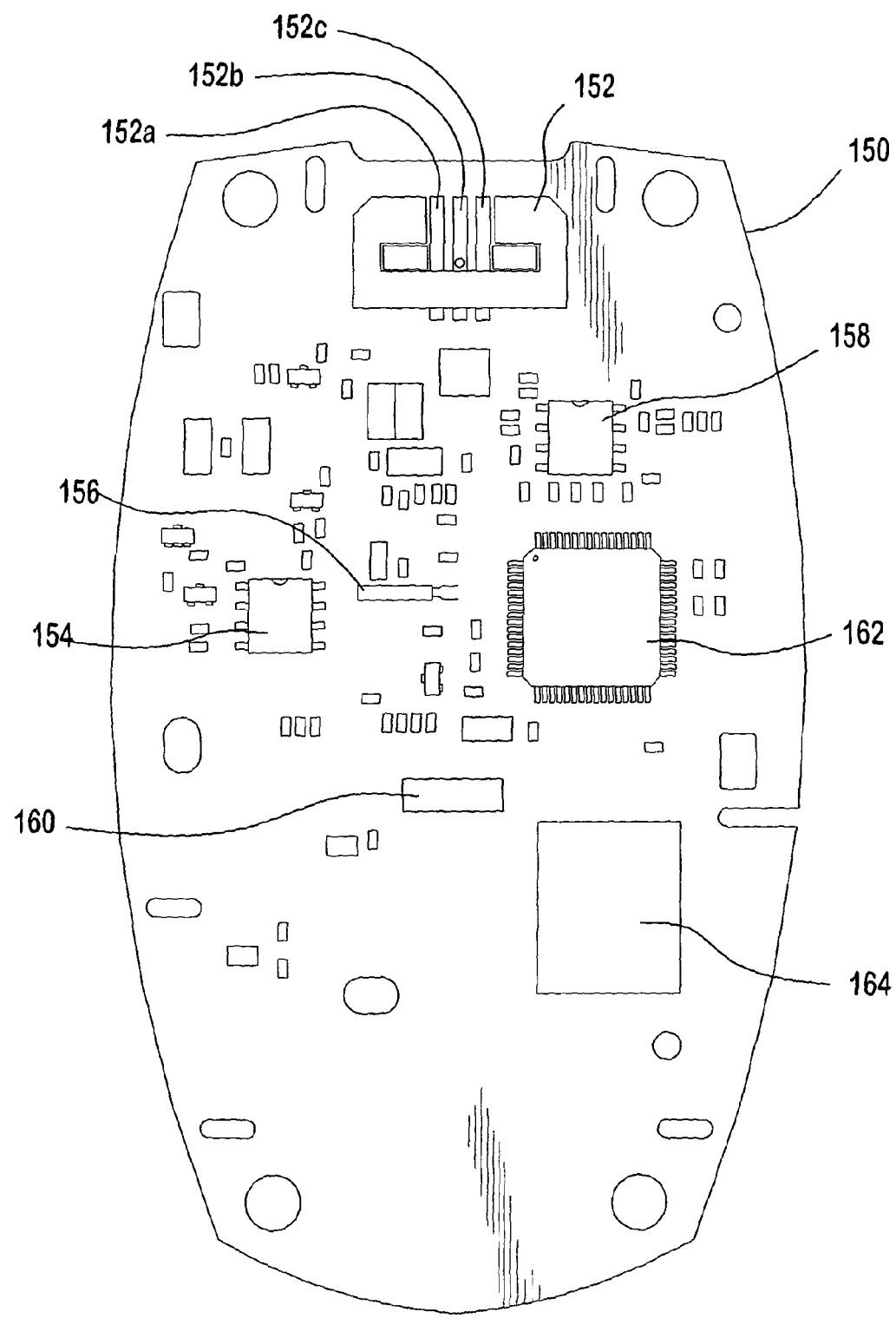
FIG. 1B illustrates an exemplary circuit board of the electrical components disposed in the analyte measurement device of FIG. 1A.

Disposed inside housing 106 includes, as shown in FIG. 1B, a circuit board 150 with a microcontroller 162 coupled to a memory 154, clock 156, operational amplifier 158, and display connector 160. The op-amp 158 and microcontroller 162 are operatively connected to a strip port connector 152 with contacts 152a, 152b, and 152b for mechanical contact with corresponding conductive tracks on the test strip 120. To facilitate communication with other data management devices, a wireless transceiver module 164 is provided to allow for bi-directional communication of data stored in the memory 154 of the unit 100. On the other side of circuit board 150 a power source in the form of a battery (not shown) is provided. A data port may also be provided. It should be noted that the meter unit 100 is preferably sized and configured to be handheld and the transceiver 164 can be for use with either or both of a short-range wireless network (e.g., BlueTooth or Wi-Fi and the like) or a longer range wireless network (e.g., GSM, CDMA, 3G and the like).

Microcontroller 162 can be electrically connected to strip port 152, operational amplifier circuit 158, first wireless module 164, display 104, non-volatile memory 154, clock 156, data port, and user interface buttons 108. Data entered via the buttons, transceiver or glucose measurement circuit can include values representative of analyte concentration, or in the context of the analyte concentration values coupled with information, which are related to the everyday lifestyle of an individual. Information, which is related to the everyday lifestyle, can include food intake, medication use, occurrence of health check-ups, and general health condition and exercise levels of an individual coupled to or "tagged" with the analyte concentration value of the user at specific time of the day or week.

Operational amplifier circuit 158 can be two or more operational amplifiers configured to provide a portion of the potentiostat function and the current measurement function. The potentiostat function can refer to the application of a test voltage between at least two electrodes of a test strip. The current function can refer to the measurement of a test current resulting from the applied test voltage to the test strip 120. The current measurement may be performed with a current-to-voltage converter. Microcontroller 162 can be in the form of a mixed signal microprocessor (MSP) such as, for example, the Texas Instrument MSP430F2419. The TI-MSP430F2419 can be configured to also perform a portion of the potentiostat function and the current measurement function. In addition, the MSP430F2419 can also include volatile and non-volatile memory. In another embodiment, many of the electronic components can be integrated with the microcontroller in the form of an application specific integrated circuit (ASIC).

Strip port 152 can be configured to form an electrical connection to the test strip. Display connector 160 can be configured to attach to display 104. Display 104 can be in the form of a liquid crystal display for reporting measured glucose levels, and for facilitating entry of lifestyle related information and for manipulation of graphical data, pictorial results and motion video. Display 104 may also include a backlight. Data port can accept a suitable connector attached to a connecting lead, thereby allowing meter unit 100 to be linked to an external device such as a personal computer. Data port can be any port that allows for transmission of data such as, for example, a serial, USB, or a parallel port. Clock 156 can be configured for measuring time and be in the form of an oscillating crystal.

Figure 2:
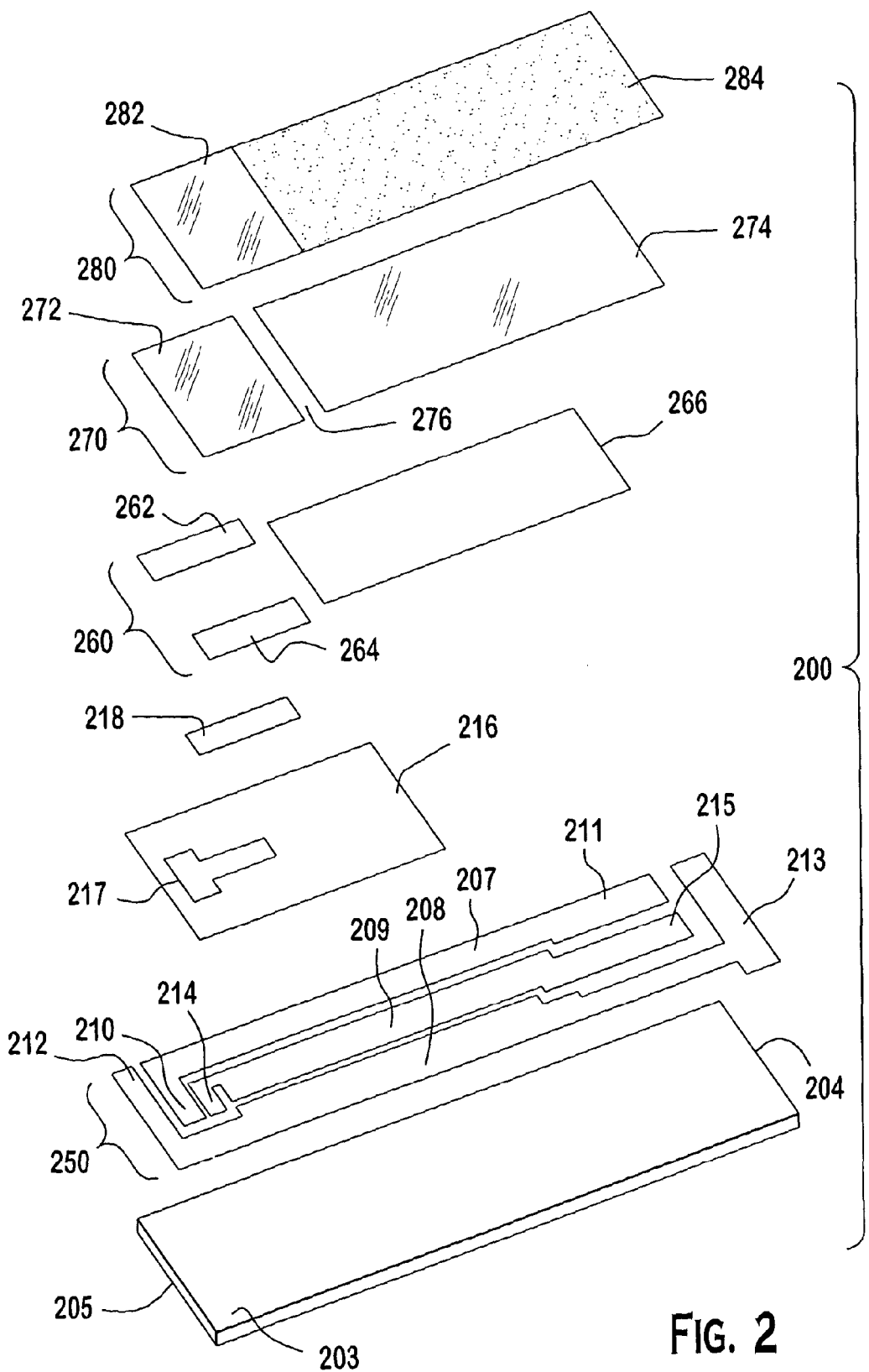
FIG. 2 illustrates an exemplary embodiment of a perspective exploded view of a test strip.
Figure 3:
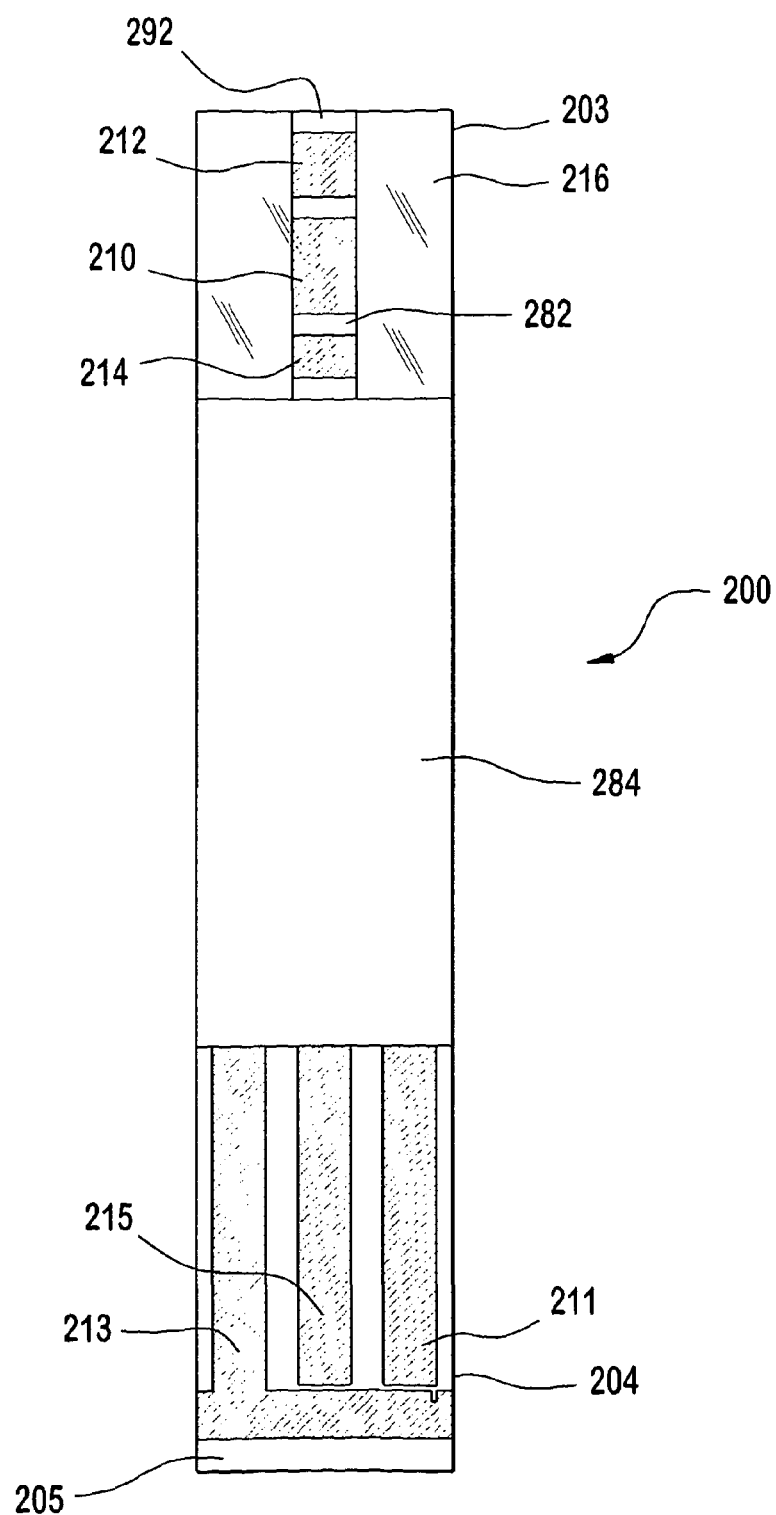
FIG. 3 illustrates an exemplary embodiment of a top view of the test strip shown in FIG. 2.

FIGS. 2 and 3 are exemplary exploded perspective and top assembled views, respectively, of test strip 120, which may include seven layers disposed on a substrate 205. The seven layers disposed on substrate 205 may be a conductive layer 250, an insulation layer 216, a reagent layer 218, an adhesive layer 260, a hydrophilic layer 270, and a top layer 280. Test strip 120 may be manufactured in a series of steps where the conductive layer 250, insulation layer 216, reagent layer 218, and adhesive layer 260 are sequentially deposited on substrate 205 using, for example, a screen-printing process. Hydrophilic layer 270 and top layer 280 may be disposed from a roll stock and laminated onto substrate 205 as either an integrated laminate or as separate layers. Test strip 120 has a distal portion 203 and a proximal portion 204, as shown in FIG. 2.

Test strip 120 may include a sample-receiving chamber 292 through which a blood sample may be drawn. Sample-receiving chamber 292 may include an inlet at a proximal end of test strip 120. An outlet or air vent is included in hydrophilic layer 270, as will be described below. A blood sample may be applied to the inlet to fill a sample-receiving chamber 292 so that an analyte concentration may be measured. The side edges of a cut-out portion of adhesive layer 260 located adjacent to reagent layer 218 defines a wall of sample-receiving chamber 292, as illustrated in FIG. 2. A bottom portion or "floor" of sample-receiving chamber 292 may include a portion of substrate 205, conductive layer 250, and insulation layer 216. A top portion or "roof" of sample-receiving chamber 292 may include distal hydrophilic portion 282.

For test strip 120, as illustrated in FIG. 2, substrate 205 may be used as a foundation for helping support subsequently applied layers. Substrate 205 may be in the form of a polyester sheet such as a polyethylene tetraphthalate (PET) material. Substrate 205 may be in a roll format, nominally 350 microns thick by 370 millimeters wide and approximately 60 meters in length.

A conductive layer 250 is required for forming electrodes that may be used for the electrochemical measurement of glucose. Conductive layer 250 may be made from a carbon ink that is screen-printed onto substrate 205. In a screen-printing process, carbon ink is loaded onto a screen and then transferred through the screen using a squeegee. The printed carbon ink may be dried using hot air at about 140° C. The carbon ink may include VAGH resin, carbon black, graphite, and one or more solvents for the resin, carbon and graphite mixture. More particularly, the carbon ink may incorporate a suitable ratio of carbon black:VAGH resin in the carbon ink.

For test strip 120, as illustrated in FIG. 2, conductive layer 250 may include a reference electrode 210, a first working electrode 212, a second working electrode 214, a reference contact pad 211, a first contact pad 213, a second contact pad 215, a reference electrode track 207, a first working electrode track 208 and a second working electrode track 209. In the embodiment shown in FIG. 2, reference electrode 210 is located in between first working electrode 212 and second electrode 214 such that cross-talk between first and second working electrodes 212 and 214 is minimized.

Conductive layer 250 may be formed from a carbon ink. Reference contact pad 211, first contact pad 213 and second contact pad 215 may be configured to electrically connect to a test meter. Reference electrode track 207 provides an electrically continuous pathway from reference electrode 210 to reference contact pad 211. Similarly, first working electrode track 208 provides an electrically continuous pathway from first working electrode 12 to first contact pad 213. Similarly, second working electrode track 209 provides an electrically continuous pathway from second working electrode 214 to second contact pad 215.

Insulation layer 216 may include an aperture 217 that exposes a portion of reference electrode 210, first working electrode 212, and second working electrode 214, which may be wetted by a liquid sample. The area of first working electrode 212, second working electrode 214, and reference electrode 210 may be defined as the area exposed to the liquid sample. In addition to defining an electrode area, insulation layer 216 prevents a liquid sample from touching the electrode tracks 207, 208, and 209. It is believed that the functional area of a working electrode should be accurately defined because the magnitude of the test current is directly proportional to the effective area of the electrode. As an example, insulation layer 216 may be Ercon E6110-116 Jet Black Insulayer™ ink that may be purchased from Ercon, Inc. The test strip at this point may be treated with plasma. The plasma is created by high voltage AC at atmospheric temperatures and pressures. The resulting plasma, consisting of ionised, highly energetic particles is swept downstream in an air current to impact the substrate. Plasma treatment is used to modify the surface of the screen-printed carbon based electrodes. This surface modification is believed to increase the electrochemical activity of the carbon surface and increases the surface energy of the printed layers allowing for better adhesion between them and subsequently printed layers. Plasma treatment is also believed to improve the electrochemistry of the carbon surface making the reaction with the mediator more ideal as part of the electrochemical reaction during a measurement cycle.

Reagent layer 218 is disposed on a portion of conductive layer 250 and insulation layer 216, as illustrated in FIG. 2. In an embodiment, two overlapping reagent layers may be printed over a portion of conductive layer 250 and insulation layer 216.

Reagent layer 218 may include chemicals such as an enzyme and a mediator which selectivity reacts with an analyte of interest and a buffer for maintaining a desired pH. For example, if glucose is to be determined in a blood sample, reagent layer 218 may include an enzyme and a mediator, along with other components necessary for functional operation. Enzymatic reagent layer 18 may include, for example, glucose oxidase, tri-sodium citrate, citric acid, polyvinyl alcohol, hydroxyl ethyl cellulose, potassium ferricyanide, antifoam, cabosil, PVPVA, and water.

Exemplary enzymes suitable for use in the reagent layer include glucose oxidase, glucose dehydrogenase with a pyrroloquinoline quinone (PQQ) co-factor and glucose dehydrogenase with a flavin adenine dinucleotide (FAD) co-factor. An exemplary mediator suitable for use in the reagent layer includes ferricyanide, which in this case is in the oxidized form. The reagent layer may be configured to physically transform glucose into an enzymatic by-product and in the process generate an amount of reduced mediator (e.g., ferrocyanide) that is proportional to the glucose concentration value. Further details regarding reagent layers, and electrochemical-based analytical test strips in general, are in U.S. Pat. No. 6,241,862, the contents of which are hereby fully incorporated by reference.

In one embodiment, the area of reagent layer 218 is sufficiently large to cover the entire area of reference electrode 210, first working electrode 212 and second working electrode 214. Reagent layer 218 includes a width and a length that is sufficiently large to at least account for the largest electrode area that may be used in test strip 120. The width of reagent layer 218 may be about 2 millimeters, which is more than double a width of rectangular aperture 217.

Adhesive layer 260 includes a first adhesive pad 262, a second adhesive pad 264 and a third adhesive pad 266 and may be disposed on test strip 120 after the deposition of reagent layer 218. Portions of adhesive layer 260 may be aligned to be immediately adjacent to, touch, or partially overlap with reagent layer 218. Adhesive layer 260 may include a water based acrylic copolymer pressure sensitive adhesive that is commercially available. Adhesive layer 260 is disposed on a portion of insulation layer 216, conductive layer 250, and substrate 205. Adhesive layer 260 binds hydrophilic layer 270 to test strip 120.

Hydrophilic layer 270 may include a distal hydrophilic portion 272 and proximal hydrophilic portion 274, as illustrated in FIG. 2. A gap 276 is included between distal hydrophilic portion 272 and proximal hydrophilic portion 274. Gap 276 serves as a side vent for air as blood fills sample-receiving chamber 292 (shown in FIG. 3). Hydrophilic layer 270 may be a polyester material having one hydrophilic surface such as an anti-fog coating, which is commercially available from 3M.

The final layer to be added to test strip 120 is top layer 280, as illustrated in FIG. 2. Top layer 280 may include a clear portion 282 and opaque portion 284. Top layer 280 is disposed on and adhered to hydrophilic layer 270. Top layer 280 may be a polyester that has an adhesive coating on one side. It should be noted that the clear portion 282 substantially overlaps distal hydrophilic portion 272, which allows a user to visually confirm that sample-receiving chamber 292 may be sufficiently filled. Opaque portion 238 helps the user observe a high degree of contrast between a colored fluid such as, for example, blood within sample-receiving chamber 292 and opaque portion 284.

In the exemplary embodiments, the measurement of glucose is based upon the specific oxidation of glucose by the flavo-enzyme glucose oxidase. The reactions which may occur in a glucose test strip are summarized below in Equations A and 2.

D-Glucose+GO(ox)→Gluconic Acid+GO(red)  (A)

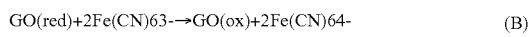

GO(red)+2Fe(CN)63-→GO(ox)+2Fe(CN)64-  (B)

As shown in Equation A, glucose is chemically transformed or oxidized to gluconic acid by the oxidized form of glucose oxidase (GO(ox)). It should be noted that GO(ox) may also be referred to as an "oxidized enzyme". During the chemical reaction in Equation A, the oxidized enzyme GO(ox) is chemically transformed or converted to its reduced state which is denoted as GO(red) (i.e., "reduced enzyme"). Next, the reduced enzyme GO(red) is again transformed or re-oxidized back to GO(ox) by reaction with Fe(CN)63- (referred to as either the oxidized mediator or ferricyanide) as shown in Equation B. During the re-generation of GO(red) back to its oxidized state GO(ox), Fe(CN)63- is reduced to Fe(CN)64- (referred to as either reduced mediator or ferrocyanide).

When the reactions set forth above are conducted with a test voltage applied between two electrodes, a test current may be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test current generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases, hence, there is a direct relationship between the test current resulting from the re-oxidation of reduced mediator and glucose concentration. In particular, the transfer of electrons across the electrical interface results in a flow of test current (2 moles of electrons for every mole of glucose that is oxidized). The test current resulting from the introduction of glucose may, therefore, be referred to as a glucose current transient or a summation of sampled current values over time.

Figure 4:
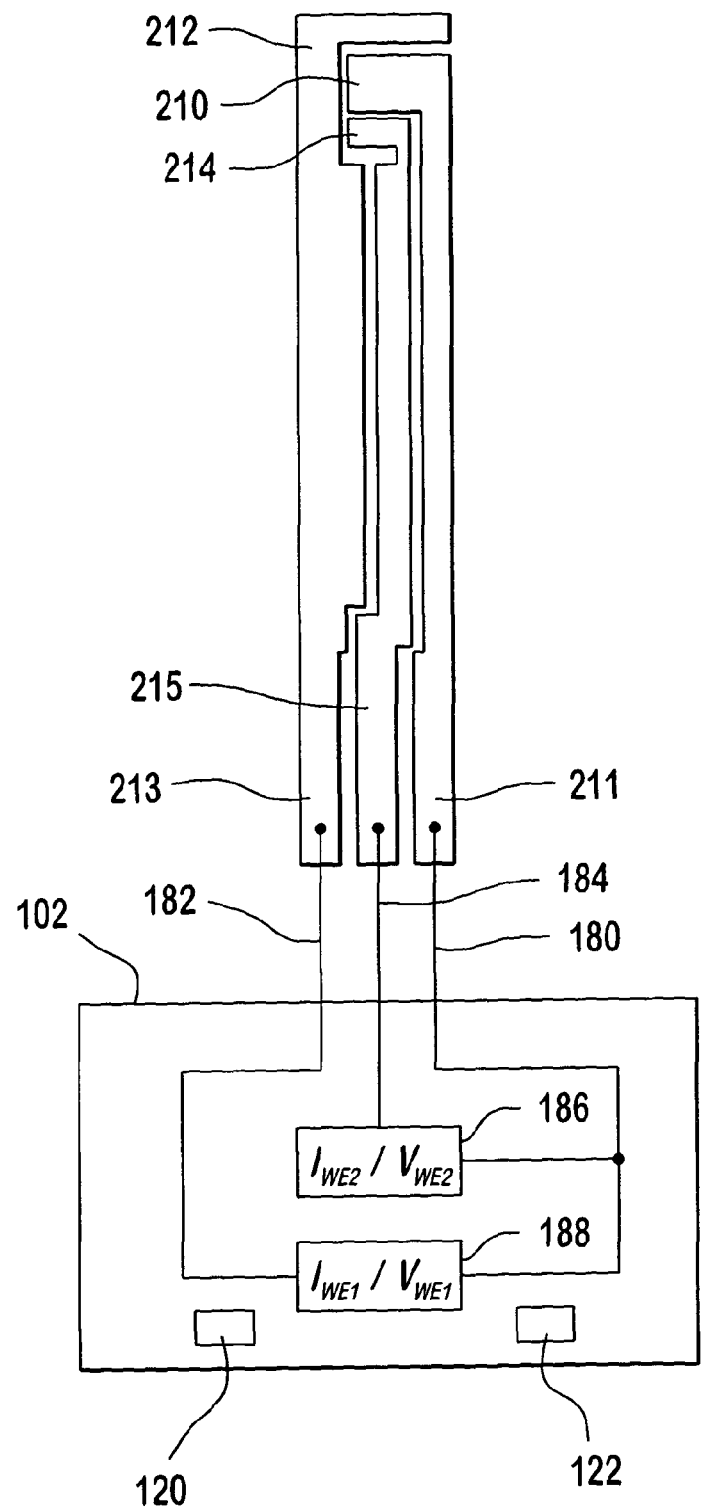
FIG. 4 illustrates an exemplary embodiment of a schematic of the functional components of the meter shown in FIG. 1A forming an electrical connection with the test strip of FIGS. 2 and 3.

FIG. 4 shows a simplified schematic of meter 102 interfacing with test strip 120. Meter 102 may include a reference connector 180, a first connector 182 and a second connector 184, which respectively form an electrical connection to reference contact 211, first contact 213 and second contact 215. The three aforementioned connectors are part of strip port 110. When performing a test, a first test voltage source 186 (from the circuit of FIG. 1B) may apply a test voltage $V_{WE2}$ between second working electrode 214 and reference electrode 210. As a result of test voltage $V_{WE2}$, meter 102 may then measure a test current $I_{WE2}$ at second working electrode. In a similar manner, a second test voltage source 188 (from the circuit of FIG. 1B) applies a test voltage $V_{WE1}$ between first working electrode 212 and reference electrode 210. As a result of test voltage $V_{WE1}$, meter 102 may then measure a test current $I_{WE1}$. In an embodiment, test voltage $V_{WE2}$ and second test voltage $V_{WE1}$ may be about equal.

Figure 5A:
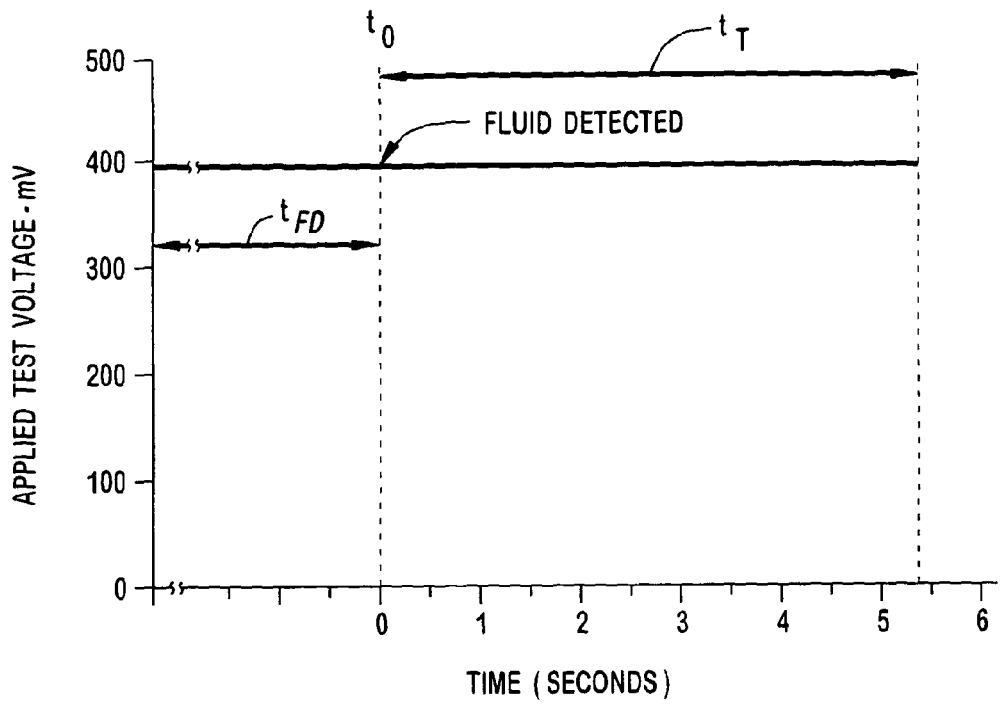
FIG. 5A illustrates an exemplary embodiment of a chart showing test voltages applied by the meter to the test strip.

FIG. 5A is an exemplary chart of a test voltage applied to test strip 120. Before a fluid sample is applied to test strip 120, test meter 102 is in a fluid detection mode in which a first test voltage of about 400 millivolts is applied between second working electrode 214 and reference electrode 210. A second test voltage of about 400 millivolts is preferably applied simultaneously between first working electrode 212 and reference electrode 210. Alternatively, the second test voltage may also be applied contemporaneously such that a time interval of the application of the first test voltage overlaps with a time interval in the application of the second test voltage. The test meter may be in a fluid detection mode during fluid detection time interval $t_{FD}$ prior to the detection of physiological fluid at time $t_0$. In the fluid detection mode, test meter 120 determines when a fluid is applied to test strip 120 in exemplary step 320 such that the fluid wets second working electrode 214 and reference electrode 210. Once test meter 120 recognizes that the physiological fluid has been applied because of, for example, a sufficient increase in the measured test current at second working electrode 214, test meter 120 assigns a zero second marker at time $t_0$ and starts the test time interval $t_T$. Upon the completion of the test time interval $t_T$, the test voltage is removed. For simplicity, FIG. 5A only shows the first test voltage applied to test strip 120.

Figure 5B:
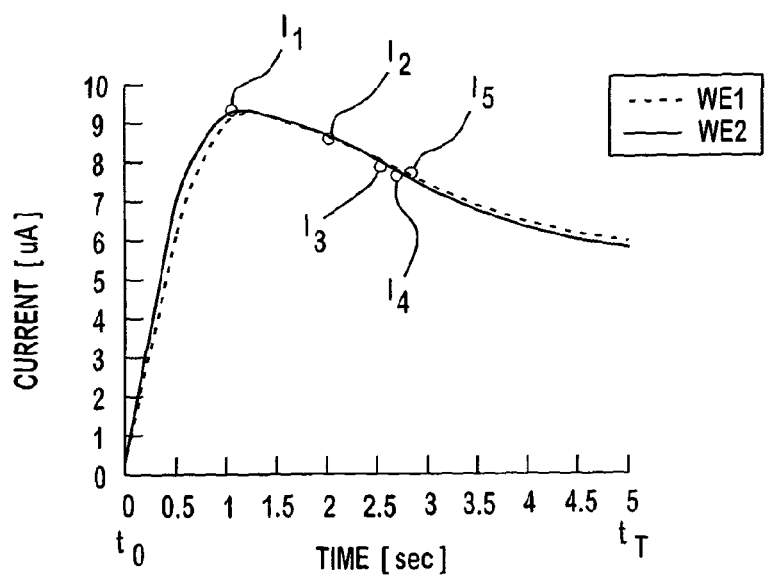
FIG. 5B illustrates an exemplary embodiment of a chart showing test currents generated when the test voltages of FIG. 5A are applied to the test strip.

FIG. 5B is an exemplary chart of current transients (i.e., the measured electrical current response in nanoamperes as a function of time) that are measured when the test voltages of FIG. 5A are applied to test strip 120. Test currents $I_i$ obtained from current transients are generally indicative of the analyte concentration in the sample as will be described in exemplary step 370 below. Referring to FIGS. 5 and 5A, in exemplary step 330, the first test voltage is applied between second working electrode 214 and reference electrode 210 and a second test voltage is applied between first working electrode 212 and reference electrode 210 at time $t_0$. In exemplary step 340, a first test current $I_1$, a second test current $I_2$, a third test current $I_3$ and a fourth test current $I_4$ are measured at times $t_2$, $t_3$, $t_4$ and $t_5$, respectively, at second working electrode 214. These currents $I_i$ where i=1, 2, 3, 4 . . . n are stored or recorded in the memory unit of the meter for analysis. In exemplary step 340, a fifth test current $I_5$ is also measured at time $t_6$ at first working electrode 212. The first and second test voltages applied to test strip 120 are generally from about +100 millivolts to about +600 millivolts. In one embodiment in which the electrodes include carbon ink and the mediator is ferricyanide, the test voltage is about +400 millivolts. Other mediator and electrode material combinations will require different test voltages. The duration of the test voltages is generally from about 2 to about 4 seconds after a reaction period and is typically about 3 seconds after a reaction period. Typically, time $t_i$ is measured relative to time $t_0$. In practice, each test current $I_i$ is the average of a set of measurements obtained over a short interval, for example, five measurements obtained at 0.01 second intervals starting at $t_{i+1}$, where i ranges from 1 to at least 6.

A hematocrit-corrected glucose concentration may be determined in conjunction with sampling of a current transient such as the one shown in FIG. 5B. The determination of the glucose concentration can be achieved with the following:

$$G = \frac{\left[\left(\frac{I_1}{I_2}\right)^{\left(a-b\frac{I_3}{I_4}\right)} xI_5\right] - \text{intercept}}{\text{slope}} \quad (1)$$

where:
G is the hematocrit-corrected glucose concentration;
$I_1$ is the first test current;
$I_2$ is the second test current;
$I_3$ is the third test current;
$I_4$ is the second test current;
$I_5$ is the third test current;
a and b are tuning parameters that are empirically derived;

intercept is an intercept value determined from a linear regression of a plot of $$\left[\left(\frac{I_1}{I_2}\right)^{\left(a-b\frac{I_3}{I_4}\right)} xI_5\right]$$

versus a reference glucose concentration; and
slope is a slope value determined from a linear regression of a plot of $$\left[\left(\frac{I_1}{I_2}\right)^{\left(a-b\frac{I_3}{I_4}\right)} xI_5\right]$$

versus the reference glucose concentration.

In one embodiment shown in FIG. 5B, first test current $I_1$ may be measured at about 0.98 seconds to about 1.00 seconds after time $t_0$, second test current $I_2$ may be measured at about 1.98 seconds to about 2.00 seconds after time $t_0$, third test current $I_3$ may be measured at about 2.43 seconds to about 2.45 seconds after time $t_0$, fourth test current may be measured at about 2.61 seconds to about 2.63 seconds after time $t_0$ and fifth test current may be measured at about 2.70 seconds to about 2.72 seconds after time $t_0$. In an embodiment, a is a first tuning parameter from about 9.9 to about 10.2 and b is a second tuning parameter from about 10.8 to about 11.2. Further details of this technique are shown and described in related U.S. Provisional Patent Application Ser. No. 61/319,470 filed on Mar. 31, 2010, the entire contents of this application are hereby incorporated by reference with a copy provided as an Appendix hereto this application.

Because the above technique uses approximately five separate sample points spread over the whole transient, specific checks are needed to eliminate waveforms that may generate very high or low results based on the sensitivities of this technique. It is believed that the general cause of these errors are varied but related to any factor that could alter the shape of the transient, particularly in areas of the transient where the exemplary embodiment samples the current transient provided by the working electrodes. Examples of phenomena that can influence transient shape would be: enzyme pad thickness, ferrocyanide impurity, flaking enzyme, partial fills and high or low temperatures. Consequently, additional checks were developed to remove anomalous results as described below.

Figure 6A:
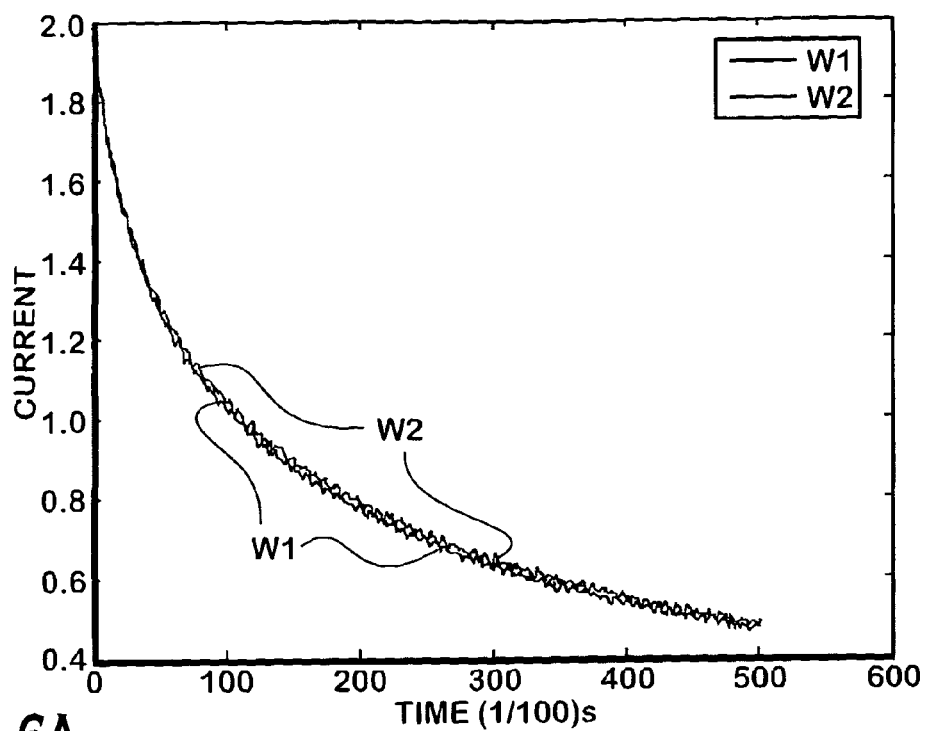
FIG. 6A illustrates a situation where a current transient of the test strip undergoes an inappropriate decay (as compared to the current transient of FIG. 5B) thereby potentially giving rise to an erroneous glucose concentration.
Figure 6B:
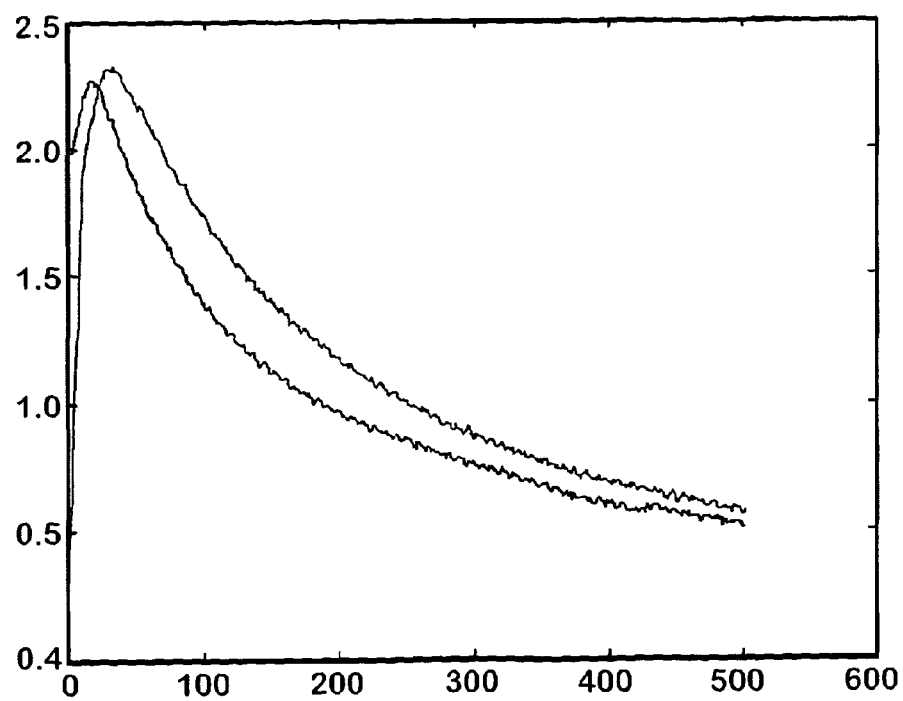
FIG. 6B illustrates a situation where a current transient of the test strip undergoes an inappropriate early peak (as compared to the current transient of FIG. 5B) thereby potentially giving rise to an erroneous glucose concentration.

In some instances, when the test voltage is applied to test strip 120, abnormal current transients as illustrated in FIGS. 6A and 6B are obtained. These abnormal current transients include no peaks due to immediate decay (FIG. 6A) or early peaks (FIG. 6B) and are believed to be caused by insufficient thickness of reagent layer 218 and/or a partial fill of sample-receiving chamber 292 with blood. A "normal" current transient should exhibit a positive rate of change in current between about zero and about 1 second, similar to FIG. 5B.

Figure 7A:
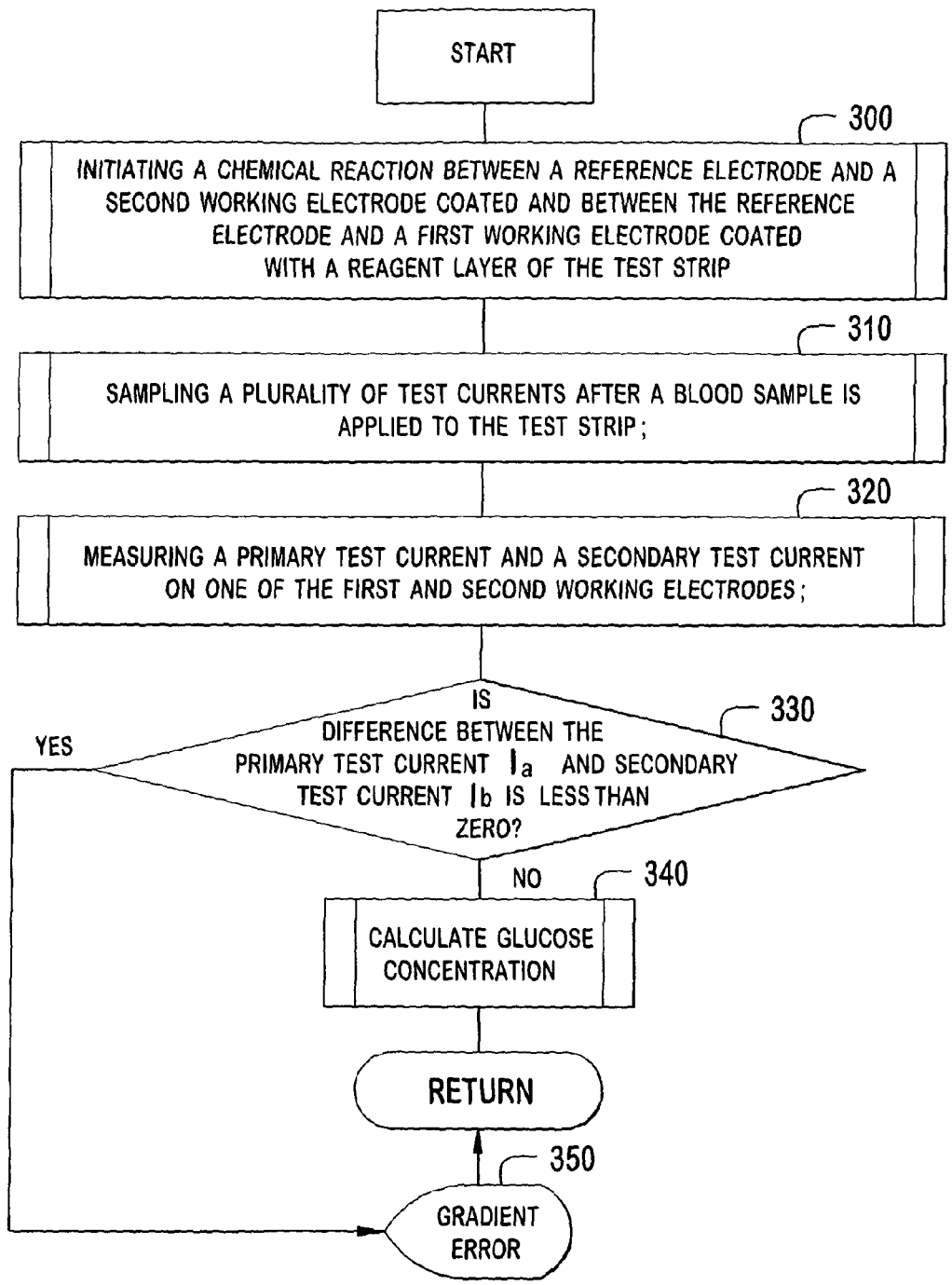
FIG. 7A illustrates a technique to trap the errors illustrated in FIGS. 6A and 6B and prevent dissemination of an erroneous glucose reading.

To account for the situations in FIGS. 6A and 6B, applicants have discovered a method, as shown in FIG. 7A, for trapping errors during a determination of a glucose concentration with the exemplary system. The method involves, in step 300, initiating a chemical reaction between a reference electrode and a second working electrode coated with a reagent layer and between the reference electrode and a first working electrode coated with a reagent layer of the test strip; in step 310, sampling a plurality of test currents after a blood sample is applied to the test strip; in step 320, measuring a primary test current and a secondary test current on one of the first and second working electrodes; in step 330, determining whether a difference between the primary test current and secondary test current is less than zero; and in step 330, upon the determining being true then in step 340, deriving or calculating a glucose concentration based on the plurality of test currents else otherwise in step 350 returning an error which may be stored in a memory of the system or displayed to the user, and causing the termination of the glucose value determination. The error in this situation is believed to be a gradient error of the sampled current transient. In this technique, the primary test current may include a current $I_a$ being sampled at about an initiation of the sampling step, which preferably is time $t_0$. The secondary test current may include a current $I_b$ being sampled at about 0.8 seconds after the initiation of the sampling step, which preferably is time $t_0$.

The deriving or calculating step for the glucose concentration may utilize Eq. (1) above, as shown and described in U.S. Provisional Patent Application Ser. No. 61/319,470 filed on Mar. 31, 2010, the entire contents of this application are hereby incorporated by reference with a copy provided as an Appendix hereto this application.

Figure 6C:
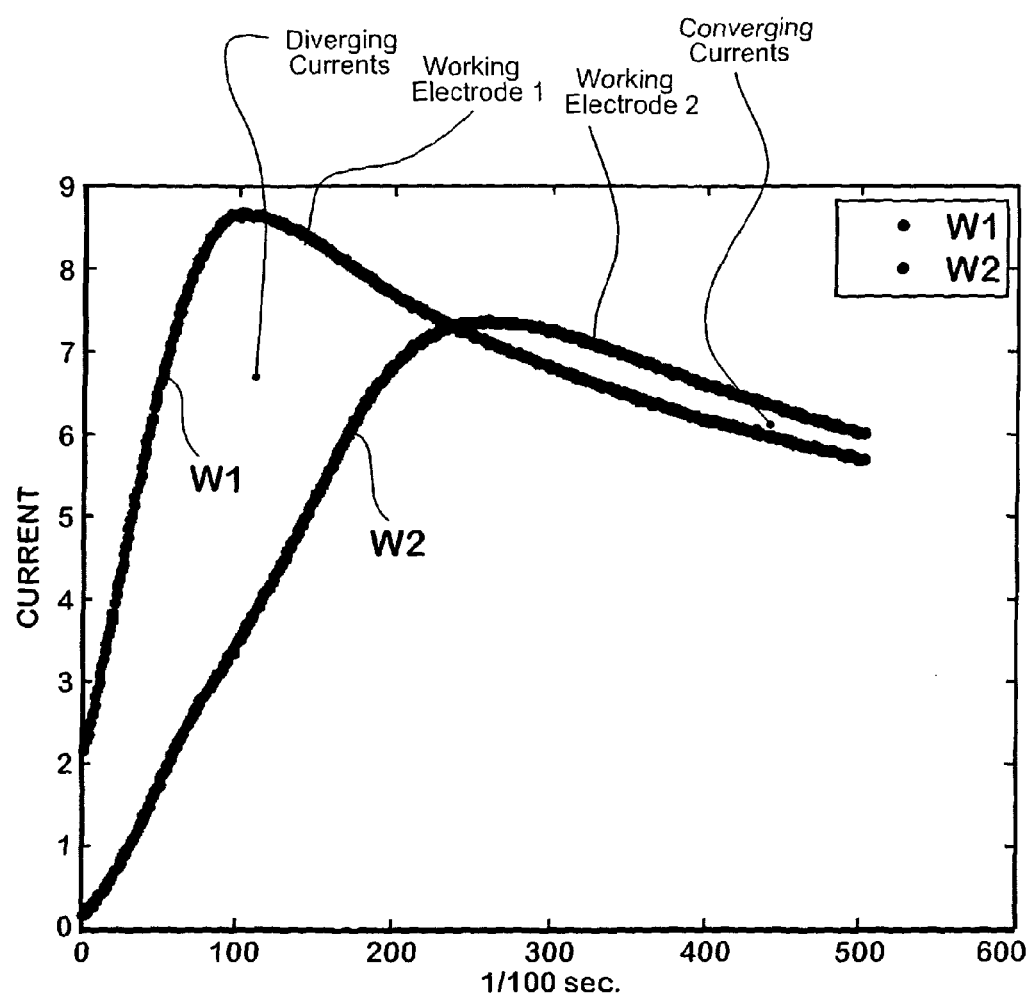
FIG. 6C illustrates a situation where the respective current transients of a first working electrode and a second working electrode do not maintain an appropriate ratio throughout the duration of the glucose measurement test.

In some instances, when the test voltage is applied to test strip 120, abnormal current transients for the respective working electrodes, as illustrated in FIG. 6C, are also obtained. In this example, the current transients for first working electrode 212 and second working electrode 214 diverge at early time periods but converge at later time periods. It is believed that this type of abnormal current transient is caused by a reagent layer 218 with an irregular thickness, from impurities in the ferrocyanide mediator and/or from a partial fill of sample-receiving chamber 292 with blood. Normal current transients at both working electrode should exhibit a ratio R of currents at about 1 second on second working electrode to first working electrode of about 1.0 to about 1.4. It is believed that the likely cause of such error is due to different speeds of diffusion at each electrode. This could result from uneven enzyme lay-down or irregularities in the strip that would make reaction at one electrode faster or slower than the other. The ratio R may be expressed as follows:

$$R = \frac{I_{WE2@tn}}{I_{WE1@tn}} \cong K$$

where
$I_{WE2@tn}$=current sampled at the second working electrode at time tn
$I_{WE1@tn}$=current sampled at the second working electrode at time tn
tn~1.1 seconds; preferably at 1.12 seconds; and
K~1 to 2, preferably 1.4 for the particular embodiments herein.

Figure 7B:
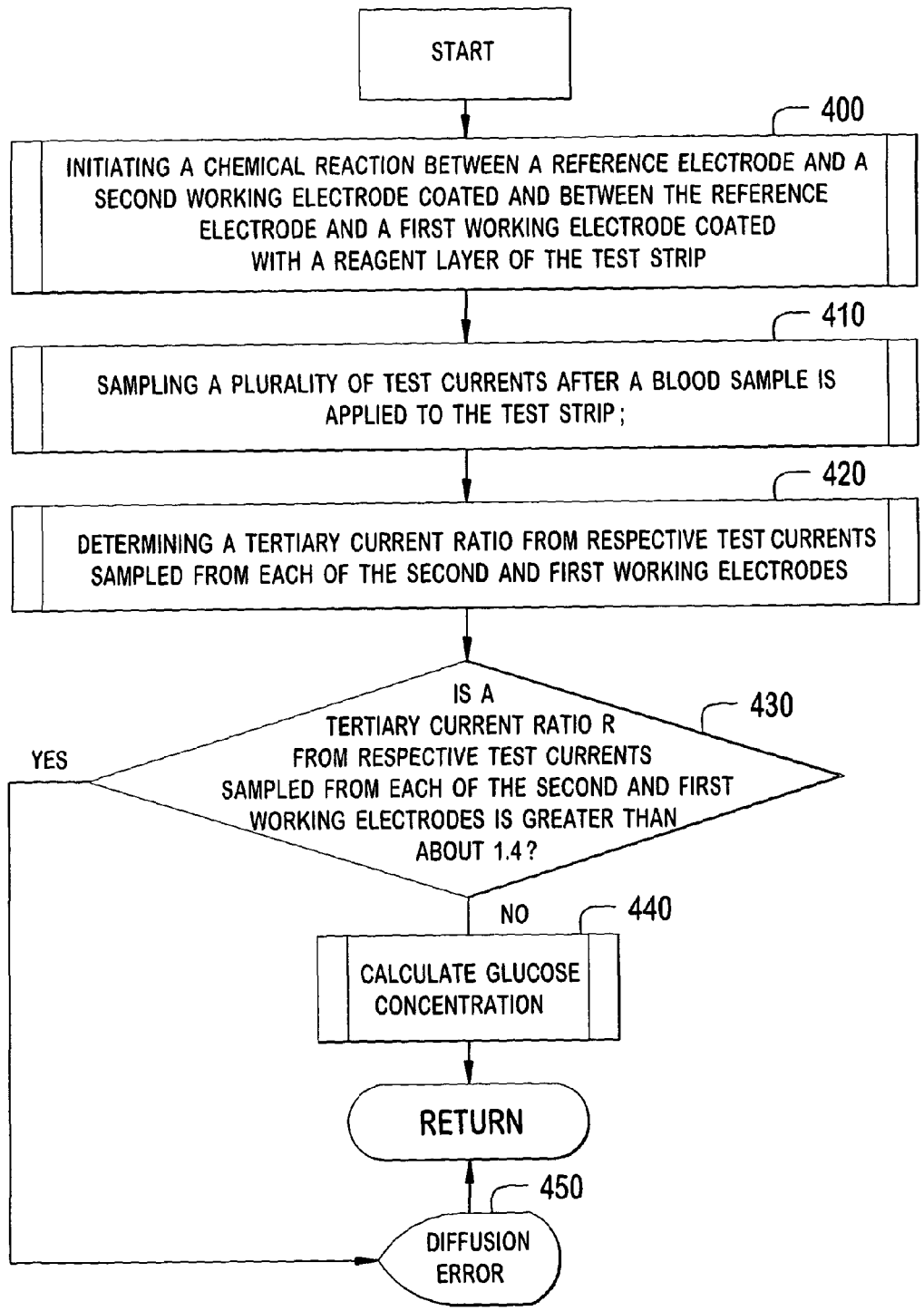
FIG. 7B illustrates a technique to trap the error illustrated in FIG. 6C and prevent dissemination of an erroneous glucose reading.

To account for the situations in FIG. 6C, applicants have discovered another method, as shown in FIG. 7B, for trapping error during a determination of a glucose concentration with the exemplary system. The method involves, in step 400, initiating a chemical reaction between a reference electrode and a second working electrode coated with a reagent layer and between the reference electrode and a first working electrode coated with a reagent layer of the test strip; in step 410, sampling a plurality of test currents after a blood sample is applied to the test strip; in step 420, determining a current ratio from respective tertiary test currents sampled from each of the second and first working electrodes; and in step 430 querying as to whether the current ratio of the second working electrode to the first working electrode is less than K, and if true, in step 440, deriving or calculating a glucose concentration based on the plurality of test currents else otherwise, in step 450, returning an error, which may be stored in a memory of the system or displayed to the user, and causing the termination of the glucose value determination.

As noted before, the deriving or calculating step for the glucose concentration may utilize Eq. (1) above, as shown and described in U.S. Provisional Patent Application Ser. No. 61/319,470 filed on Mar. 31, 2010, the entire contents of this application are hereby incorporated by reference into this application.

It is noted that both techniques illustrated exemplarily in FIGS. 7A and 7B may be combined into a single error trapping method, as shown exemplarily in FIG. 7C. This combined method may be carried out, as shown in step 500, initiating a chemical reaction between a reference electrode and a second working electrode coated with a reagent layer and between the reference electrode and a first working electrode coated with a reagent layer of the test strip; in step 510, sampling a plurality of test currents after a blood sample is applied to the test strip; in step 520, measuring a primary test current and a secondary test current on one of the first and second working electrodes; in step 530, determining a current ratio from respective tertiary test currents sampled from each of the second and first working electrodes; in step 540, determining whether a difference between the primary test current and secondary test current is less than zero; in step 550, evaluating whether a current ratio from respective tertiary test currents sampled from each of the second and first working electrodes is greater than K; and upon either or both of the determining step 540 or evaluating step 550 being true, returning an error otherwise in step 560, deriving or calculating a glucose concentration based on the plurality of sampled or measured test currents.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method for determining a glucose concentration with a system having a test strip and a meter having a test circuit including a microprocessor, the method comprising:
   initiating a chemical reaction between a reference electrode and a second working electrode coated with a reagent layer and between the reference electrode and a first working electrode coated with a reagent layer of the test strip;
   measuring a primary test current and a secondary test current on one of the first and second working electrodes;

determining whether a difference between the primary test current and secondary test current is less than zero;

if the difference between the primary test current and secondary test current is less than zero, then deriving a glucose concentration based on a plurality of test currents in which the plurality of measured test currents comprises first, second, third, fourth, and fifth test currents and K comprises a value from about 1.0 to about 2.0, and wherein the deriving comprises calculating a value representative of glucose concentration with an equation of the form:

$$G = \frac{\left[\left(\frac{I_1}{I_2}\right)^{\left(a-b\frac{I_3}{I_4}\right)} x I_5\right] - \text{intercept}}{\text{slope}}$$

where:
G comprises the glucose concentration;
$I_1$ comprises the first test current;
$I_2$ comprises the second test current;
$I_3$ comprises the third test current;
$I_4$ comprises the fourth test current;
$I_5$ comprises the fifth test current;
a comprises a first tuning parameter and b comprises a second tuning parameter;
intercept comprises an intercept value determined from a linear regression of a plot of $$\left[\left(\frac{I_1}{I_2}\right)^{\left(a-b\frac{I_3}{I_4}\right)} x I_5\right]$$

versus a reference glucose concentration; and
slope comprises a slope value determined from a linear regression of a plot of $$\left[\left(\frac{I_1}{I_2}\right)^{\left(a-b\frac{I_3}{I_4}\right)} x I_5\right]$$

versus the reference glucose concentration; and
if the difference between the primary test current and secondary test current is not less than zero, then returning an error.

2. The method of claim 1, in which the primary test current comprises a current being sampled at about an initiation of the measuring step.

3. The method of claim 1, in which the secondary test current comprises a current being sampled at about 0.8 seconds after the initiation of the measuring step.

4. The method of claim 1, in which K comprises a value from about 1 to about 1.4.

5. The method of claim 1, in which K comprises a value of about 1.4.

6. The method of claim 1, in which the first test current comprises a test current measured from about 0.98 to about 1.00 seconds after initiation of the measuring.

7. The method of claim 1, in which the second current comprises a test current measured from about 1.98 to about 2.00 seconds after initiation of the measuring.

8. The method of claim 1, in which the third current comprises a test current measured from about 2.43 to about 2.45 seconds after initiation of the measuring.

9. The method of claim 1, in which the fourth current comprises a test current measured from about 2.61 to about 2.63 seconds after initiation of the measuring.

10. The method of claim 1, in which the fifth current comprises a test current measured from about 2.70 to about 2.72 seconds after initiation of the measuring.

11. The method of claim 1, in which first tuning parameter comprises a value from about 9.9 to about 10.2 and second tuning parameter comprises a value from about 10.8 to about 11.2.

12. A method for determining a glucose concentration with a system having a test strip and a meter having a test circuit including a microprocessor, the method comprising:
initiating a chemical reaction between a reference electrode and a second working electrode coated with a reagent layer and between the reference electrode and a first working electrode coated with a reagent layer of the test strip;
sampling a plurality of test currents after a blood sample is applied to the test strip;
determining a current ratio from respective tertiary test currents sampled from each of the second and first working electrodes;
querying as to whether the current ratio of the second working electrode to the first working electrode is less than about K, and if the current ratio of the second working electrode to the first working electrode is less than about K, then deriving a glucose concentration based on the plurality of test currents in which the plurality of measured or sampled test currents comprises first, second, third, fourth, and fifth test currents and K comprises a constant and wherein the deriving comprises calculating a value representative of glucose concentration with an equation of the form:

$$G = \frac{\left[\left(\frac{I_1}{I_2}\right)^{\left(a-b\frac{I_3}{I_4}\right)} x I_5\right] - \text{intercept}}{\text{slope}}$$

where:
G comprises the glucose concentration;
$I_1$ comprises the first test current;
$I_2$ comprises the second test current;
$I_3$ comprises the third test current;
$I_4$ comprises the fourth test current;
$I_5$ comprises the fifth test current;
a comprises a first tuning parameter and b comprises a second tuning parameter;
intercept comprises an intercept value determined from a linear regression of a plot of $$\left[\left(\frac{I_1}{I_2}\right)^{\left(a-b\frac{I_3}{I_4}\right)} x I_5\right]$$

versus a reference glucose concentration; and
slope comprises a slope value determined from a linear regression of a plot of $$\left[\left(\frac{I_1}{I_2}\right)^{\left(a-b\frac{I_3}{I_4}\right)} x I_5\right]$$

versus the reference glucose concentration; and
if the current ratio of the second working electrode to the first working electrode is not less than about K, then returning an error.

13. The method of claim 12, in which the first test current comprises a test current measured from about 0.98 to about 1.00 seconds after initiation of the measuring.

14. The method of claim 12, in which the second current comprises a test current measured from about 1.98 to about 2.00 seconds after initiation of the measuring.

15. The method of claim 12, in which the third current comprises a test current measured from about 2.43 to about 2.45 seconds after initiation of the measuring.

16. The method of claim 12, in which the fourth current comprises a test current measured from about 2.61 to about 2.63 seconds after initiation of the measuring.

17. The method of claim 12, in which the fifth current comprises a test current measured from about 2.70 to about 2.72 seconds after initiation of the measuring.

18. The method of claim 12, in which first tuning parameter comprises a value from about 9.9 to about 10.2 and second tuning parameter comprises a value from about 10.8 to about 11.2.

19. A method for determining a glucose concentration with a system having a test strip and a meter having a test circuit including a microprocessor, the method comprising:
initiating a chemical reaction between a reference electrode and a second working electrode coated with a reagent layer and between the reference electrode and a first working electrode coated with a reagent layer of the test strip;
measuring a primary test current and a secondary test current on one of the first and second working electrodes;
determining whether a difference between the primary test current and secondary test current is less than zero;
determining a current ratio from respective tertiary test currents sampled from each of the second and first working electrodes;
evaluating whether a current ratio from respective tertiary test currents sampled from each of the second and first working electrodes is greater than about K, in which K comprises a constant; and
upon either or both of the difference being less than zero or the current ratio being greater than about K, returning an error otherwise deriving a glucose concentration based on the plurality of test currents in which the plurality of measured or sampled test currents comprises first, second, third, fourth, and fifth test currents, K is between about 1.0 and 1.4, and wherein the deriving comprises calculating a value representative of glucose concentration with an equation of the form:

$$G = \frac{\left[\left(\frac{I_1}{I_2}\right)^{\left(a-b\frac{I_3}{I_4}\right)} xI_5\right] - \text{intercept}}{\text{slope}}$$

where:
G comprises the glucose concentration;
$I_1$ comprises the first test current;
$I_2$ comprises the second test current;
$I_3$ comprises the third test current;
$I_4$ comprises the fourth test current;
$I_5$ comprises the fifth test current;
a comprises a first tuning parameter and b comprises a second tuning parameter;
intercept comprises an intercept value determined from a linear regression of a plot of $$\left[\left(\frac{I_1}{I_2}\right)^{\left(a-b\frac{I_3}{I_4}\right)} xI_5\right]$$

versus a reference glucose concentration; and
slope comprises a slope value determined from a linear regression of a plot of $$\left[\left(\frac{I_1}{I_2}\right)^{\left(a-b\frac{I_3}{I_4}\right)} xI_5\right]$$

versus the reference glucose concentration.

20. The method of claim 19, in which the first test current comprises a test current measured from about 0.98 to about 1.00 seconds after initiation of the measuring.

21. The method of claim 19, in which the second current comprises a test current measured from about 1.98 to about 2.00 seconds after initiation of the measuring.

22. The method of claim 19, in which the third current comprises a test current measured from about 2.43 to about 2.45 seconds after initiation of the measuring.

23. The method of claim 19, in which the fourth current comprises a test current measured from about 2.61 to about 2.63 seconds after initiation of the measuring.

24. The method of claim 19, in which the fifth current comprises a test current measured from about 2.70 to about 2.72 seconds after initiation of the measuring.

25. The method of claim 19, in which first tuning parameter comprises a value from about 9.9 to about 10.2 and second tuning parameter comprises a value from about 10.8 to about 11.2.

* * * * *